(12) United States Patent
Reiley

(10) Patent No.: US 9,561,063 B2
(45) Date of Patent: Feb. 7, 2017

(54) SYSTEMS AND METHODS FOR THE FIXATION OR FUSION OF BONE

(75) Inventor: Mark A. Reiley, Piedmont, CA (US)

(73) Assignee: SI-Bone Inc., San Jose, CA (US)

( * ) Notice: Subject to any disclaimer, the term of this patent is extended or adjusted under 35 U.S.C. 154(b) by 0 days.

(21) Appl. No.: 13/078,530

(22) Filed: Apr. 1, 2011

(65) Prior Publication Data

US 2011/0184478 A1 Jul. 28, 2011

Related U.S. Application Data

(60) Continuation of application No. 12/804,516, filed on Jul. 22, 2010, now Pat. No. 8,202,305, which is a
(Continued)

(51) Int. Cl.
*A61F 2/46* (2006.01)
*A61B 17/86* (2006.01)
(Continued)

(52) U.S. Cl.
CPC ......... *A61B 17/864* (2013.01); *A61B 17/1615* (2013.01); *A61B 17/68* (2013.01); *A61B 17/70* (2013.01); *A61B 17/846* (2013.01); *A61B 17/866* (2013.01); *A61B 17/8625* (2013.01); *A61B 17/8685* (2013.01); *A61F 2/4455* (2013.01); *A61F 2/0077* (2013.01); *A61F 2/28* (2013.01); *A61F 2/30767* (2013.01); *A61F 2/447* (2013.01); *A61F 2/4465* (2013.01); *A61F 2002/305* (2013.01); *A61F 2002/3023* (2013.01); *A61F 2002/30062* (2013.01); *A61F 2002/3082* (2013.01); *A61F 2002/3085* (2013.01); *A61F 2002/30156* (2013.01);
(Continued)

(58) Field of Classification Search
CPC ..... A61B 17/72; A61B 17/58; A61B 17/7216; A61B 17/7225
USPC ................... 606/246–279, 62, 86 R, 95, 105
See application file for complete search history.

(56) References Cited

U.S. PATENT DOCUMENTS 1,951,278 A 3/1934 Ericsson
2,136,471 A 11/1938 Schneider
(Continued)

FOREIGN PATENT DOCUMENTS

CN 1128944 A 8/1996
CN 1190882 A 8/1998
(Continued)

OTHER PUBLICATIONS

Reiley, Mark A.; U.S. Appl. No. 12/357,483 entitled "Systems and methods for the fixation or fusion of bone in the hand and wrist," filed Jan. 22, 2009 (abandoned).
(Continued)

*Primary Examiner* — Ellen C Hammond
*Assistant Examiner* — Christina Negrellirodrigue
(74) *Attorney, Agent, or Firm* — Shay Glenn LLP

(57) ABSTRACT

A joint between two bone segments is fused by passing an elongated, rectilinear bone fusion device over a guide pin across the joint and into tight engagement within bores formed in the bone segments, to thereby restrict movement of the elongated bone fusion device across the joint. The elongated, rectilinear bone fusion device also provides bony in-growth within the bores along the exterior surface of the bone fusion device.

15 Claims, 11 Drawing Sheets

Related U.S. Application Data division of application No. 11/136,141, filed on May 24, 2005, now Pat. No. 7,922,765, which is a continuation-in-part of application No. 10/914,629, filed on Aug. 9, 2004, now abandoned.

(51) Int. Cl.
   *A61B 17/16* (2006.01)
   *A61B 17/68* (2006.01)
   *A61F 2/44* (2006.01)
   *A61B 17/84* (2006.01)
   *A61B 17/70* (2006.01)
   *A61F 2/00* (2006.01)
   *A61F 2/28* (2006.01)
   *A61F 2/30* (2006.01)
   *A61F 2/42* (2006.01)

(52) U.S. Cl.
   CPC .............. *A61F 2002/30179* (2013.01); *A61F 2002/30235* (2013.01); *A61F 2002/30405* (2013.01); *A61F 2002/30576* (2013.01); *A61F 2002/30604* (2013.01); *A61F 2002/30622* (2013.01); *A61F 2002/30777* (2013.01); *A61F 2002/30785* (2013.01); *A61F 2002/30787* (2013.01); *A61F 2002/30841* (2013.01); *A61F 2002/4238* (2013.01); *A61F 2002/448* (2013.01); *A61F 2210/0004* (2013.01); *A61F 2220/0025* (2013.01); *A61F 2230/0023* (2013.01); *A61F 2230/0058* (2013.01); *A61F 2230/0069* (2013.01); *A61F 2310/00017* (2013.01); *A61F 2310/00023* (2013.01); *A61F 2310/00029* (2013.01); *A61F 2310/0097* (2013.01); *A61F 2310/00131* (2013.01); *A61F 2310/00179* (2013.01); *A61F 2310/00329* (2013.01); *A61F 2310/00353* (2013.01); *A61F 2310/00359* (2013.01); *A61F 2310/00796* (2013.01)

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 4,059,115 A | 11/1977 | Jumashev et al. |
| 4,156,943 A | 6/1979 | Collier |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A * | 12/1986 | Harder et al. ................ 606/62 |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A * | 11/1989 | Brantigan ................ 623/17.11 |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,981,481 A | 1/1991 | Kranz et al. |
| 5,034,011 A | 7/1991 | Howland |
| 5,035,697 A | 7/1991 | Frigg |
| 5,041,118 A | 8/1991 | Wasilewski |
| 5,053,035 A | 10/1991 | McClaren |
| 5,059,193 A | 10/1991 | Kuslich |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A * | 7/1995 | Brinker ................ A61B 17/72 606/62 |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,743,912 A | 4/1998 | LaHille et al. |
| 5,759,035 A | 6/1998 | Ricci |
| 5,766,174 A | 6/1998 | Perry |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 5,968,047 A | 10/1999 | Reed |
| 6,010,507 A | 1/2000 | Rudloff |
| 6,015,409 A | 1/2000 | Jackson |
| 6,053,916 A | 4/2000 | Moore |
| 6,056,749 A | 5/2000 | Kuslich |
| 6,086,589 A | 7/2000 | Kuslich et al. |
| 6,096,080 A | 8/2000 | Nicholson et al. |
| 6,120,504 A | 9/2000 | Brumback et al. |
| 6,143,031 A | 11/2000 | Knothe et al. |
| 6,197,062 B1 | 3/2001 | Fenlin |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |

(56) References Cited

U.S. PATENT DOCUMENTS

| | | | |
|---|---|---|---|
| 6,302,914 B1 * | 10/2001 | Michelson | A61F 2/44 623/17.16 |
| 6,306,140 B1 | 10/2001 | Siddiqui | |
| 6,319,253 B1 | 11/2001 | Ackeret et al. | |
| 6,409,768 B1 | 6/2002 | Tepic et al. | |
| 6,451,020 B1 | 9/2002 | Zucherman et al. | |
| 6,471,707 B1 | 10/2002 | Miller et al. | |
| 6,485,518 B1 | 11/2002 | Cornwall et al. | |
| 6,497,707 B1 | 12/2002 | Bowman et al. | |
| 6,517,541 B1 | 2/2003 | Sesic | |
| 6,520,969 B2 | 2/2003 | Lambrecht et al. | |
| 6,524,314 B1 | 2/2003 | Dean et al. | |
| 6,527,775 B1 | 3/2003 | Warburton | |
| 6,558,386 B1 | 5/2003 | Cragg | |
| 6,565,566 B1 | 5/2003 | Wagner et al. | |
| 6,575,899 B1 | 6/2003 | Foley et al. | |
| 6,575,991 B1 | 6/2003 | Chesbrough et al. | |
| 6,579,293 B1 | 6/2003 | Chandran | |
| 6,582,431 B1 | 6/2003 | Ray | |
| 6,595,998 B2 | 7/2003 | Johnson et al. | |
| 6,602,293 B1 | 8/2003 | Biermann et al. | |
| 6,605,090 B1 | 8/2003 | Trieu et al. | |
| 6,607,530 B1 | 8/2003 | Carl et al. | |
| 6,620,163 B1 | 9/2003 | Michelson | |
| 6,635,059 B2 | 10/2003 | Randall et al. | |
| 6,666,868 B2 | 12/2003 | Fallin | |
| 6,669,529 B1 | 12/2003 | Scaries | |
| 6,673,075 B2 | 1/2004 | Santilli | |
| 6,692,501 B2 | 2/2004 | Michelson | |
| 6,723,099 B1 | 4/2004 | Goshert | |
| 6,740,118 B2 | 5/2004 | Eisermann et al. | |
| 6,743,257 B2 | 6/2004 | Castro | |
| D493,533 S | 7/2004 | Blain | |
| 6,793,656 B1 | 9/2004 | Mathews | |
| 6,827,740 B1 * | 12/2004 | Michelson | A61F 2/4455 623/17.11 |
| 6,984,235 B2 | 1/2006 | Huebner | |
| 6,991,461 B2 | 1/2006 | Gittleman | |
| 7,118,579 B2 | 10/2006 | Michelson | |
| 7,175,663 B1 | 2/2007 | Stone | |
| 7,211,085 B2 | 5/2007 | Michelson | |
| 7,223,269 B2 | 5/2007 | Chappuis | |
| 7,335,205 B2 | 2/2008 | Aeschlimann et al. | |
| 7,338,500 B2 | 3/2008 | Chappuis | |
| 7,452,359 B1 | 11/2008 | Michelson | |
| 7,452,369 B2 | 11/2008 | Barry | |
| 7,481,831 B2 | 1/2009 | Bonutti | |
| 7,527,649 B1 | 5/2009 | Blain | |
| 7,534,254 B1 | 5/2009 | Michelson | |
| 7,537,616 B1 | 5/2009 | Branch et al. | |
| 7,569,054 B2 | 8/2009 | Michelson | |
| 7,569,059 B2 | 8/2009 | Cerundolo | |
| 7,601,155 B2 | 10/2009 | Petersen | |
| 7,648,509 B2 | 1/2010 | Stark | |
| 7,686,805 B2 | 3/2010 | Michelson | |
| 7,699,852 B2 | 4/2010 | Frankel et al. | |
| 7,708,761 B2 | 5/2010 | Petersen | |
| 7,758,646 B2 | 7/2010 | Khandkar et al. | |
| 7,857,832 B2 | 12/2010 | Culbert et al. | |
| 7,887,565 B2 | 2/2011 | Michelson | |
| 7,909,832 B2 | 3/2011 | Michelson | |
| 7,922,765 B2 | 4/2011 | Reiley | |
| 7,942,879 B2 | 5/2011 | Christie et al. | |
| 8,062,365 B2 | 11/2011 | Schwab | |
| 8,066,705 B2 | 11/2011 | Michelson | |
| 8,066,709 B2 | 11/2011 | Michelson | |
| 8,142,481 B2 | 3/2012 | Warnick | |
| 8,672,986 B2 | 3/2014 | Klaue et al. | |
| 8,945,190 B2 | 2/2015 | Culbert et al. | |
| 2001/0012942 A1 | 8/2001 | Estes et al. | |
| 2001/0046518 A1 | 11/2001 | Sawhney | |
| 2001/0047207 A1 | 11/2001 | Michelson | |
| 2001/0049529 A1 | 12/2001 | Cachia et al. | |
| 2002/0038123 A1 * | 3/2002 | Visotsky | A61B 17/8095 606/304 |
| 2002/0049497 A1 | 4/2002 | Mason | |
| 2002/0077641 A1 | 6/2002 | Michelson | |
| 2002/0082598 A1 * | 6/2002 | Teitelbaum | A61B 17/1671 606/86 A |
| 2002/0120275 A1 | 8/2002 | Schmieding et al. | |
| 2002/0128652 A1 | 9/2002 | Ferree | |
| 2002/0143334 A1 | 10/2002 | von Hoffmann et al. | |
| 2002/0143335 A1 | 10/2002 | von Hoffmann et al. | |
| 2002/0151903 A1 | 10/2002 | Takei et al. | |
| 2002/0183858 A1 | 12/2002 | Contiliano et al. | |
| 2002/0198527 A1 | 12/2002 | Mückter | |
| 2003/0018336 A1 | 1/2003 | Vandewalle | |
| 2003/0032961 A1 * | 2/2003 | Pelo et al. | 606/72 |
| 2003/0050642 A1 | 3/2003 | Schmieding et al. | |
| 2003/0065332 A1 | 4/2003 | TenHuisen et al. | |
| 2003/0074000 A1 | 4/2003 | Roth et al. | |
| 2003/0078660 A1 | 4/2003 | Clifford et al. | |
| 2003/0083668 A1 | 5/2003 | Rogers et al. | |
| 2003/0083688 A1 | 5/2003 | Simonson | |
| 2003/0097131 A1 | 5/2003 | Schon et al. | |
| 2003/0139815 A1 | 7/2003 | Grooms et al. | |
| 2003/0181982 A1 | 9/2003 | Kuslich | |
| 2003/0199983 A1 | 10/2003 | Michelson | |
| 2003/0229358 A1 | 12/2003 | Errico et al. | |
| 2003/0233146 A1 | 12/2003 | Grinberg et al. | |
| 2003/0233147 A1 | 12/2003 | Nicholson et al. | |
| 2004/0010315 A1 | 1/2004 | Song | |
| 2004/0024458 A1 | 2/2004 | Senegas et al. | |
| 2004/0034422 A1 | 2/2004 | Errico et al. | |
| 2004/0073216 A1 | 4/2004 | Lieberman | |
| 2004/0073314 A1 | 4/2004 | White et al. | |
| 2004/0082955 A1 | 4/2004 | Zirkle | |
| 2004/0087948 A1 | 5/2004 | Suddaby | |
| 2004/0097927 A1 | 5/2004 | Yeung et al. | |
| 2004/0106925 A1 | 6/2004 | Culbert | |
| 2004/0117022 A1 | 6/2004 | Marnay et al. | |
| 2004/0127990 A1 * | 7/2004 | Bartish et al. | 623/17.11 |
| 2004/0138750 A1 | 7/2004 | Mitchell | |
| 2004/0138753 A1 | 7/2004 | Ferree | |
| 2004/0147929 A1 | 7/2004 | Biedermann et al. | |
| 2004/0176287 A1 | 9/2004 | Harrison et al. | |
| 2004/0176853 A1 | 9/2004 | Sennett et al. | |
| 2004/0181282 A1 | 9/2004 | Zucherman et al. | |
| 2004/0210221 A1 | 10/2004 | Kozak et al. | |
| 2004/0225360 A1 | 11/2004 | Malone | |
| 2004/0230305 A1 | 11/2004 | Gorensek et al. | |
| 2004/0260286 A1 | 12/2004 | Ferree | |
| 2004/0267369 A1 | 12/2004 | Lyons et al. | |
| 2005/0015059 A1 | 1/2005 | Sweeney | |
| 2005/0015146 A1 | 1/2005 | Louis et al. | |
| 2005/0033435 A1 | 2/2005 | Belliard et al. | |
| 2005/0049590 A1 | 3/2005 | Alleyne et al. | |
| 2005/0055023 A1 | 3/2005 | Sohngen et al. | |
| 2005/0075641 A1 | 4/2005 | Singhatat et al. | |
| 2005/0080415 A1 | 4/2005 | Keyer et al. | |
| 2005/0107878 A1 | 5/2005 | Conchy | |
| 2005/0124993 A1 | 6/2005 | Chappuis | |
| 2005/0131409 A1 | 6/2005 | Chervitz et al. | |
| 2005/0137605 A1 | 6/2005 | Assell et al. | |
| 2005/0149192 A1 | 7/2005 | Zucherman et al. | |
| 2005/0159749 A1 | 7/2005 | Levy et al. | |
| 2005/0165398 A1 | 7/2005 | Reiley | |
| 2005/0192572 A1 | 9/2005 | Abdelgany et al. | |
| 2005/0228384 A1 | 10/2005 | Zucherman et al. | |
| 2005/0246021 A1 | 11/2005 | Ringeisen et al. | |
| 2005/0251146 A1 | 11/2005 | Martz et al. | |
| 2006/0036247 A1 | 2/2006 | Michelson | |
| 2006/0036251 A1 | 2/2006 | Reiley | |
| 2006/0054171 A1 | 3/2006 | Dall | |
| 2006/0058793 A1 | 3/2006 | Michelson | |
| 2006/0058800 A1 | 3/2006 | Ainsworth et al. | |
| 2006/0062825 A1 | 3/2006 | Maccecchini | |
| 2006/0084986 A1 | 4/2006 | Grinberg et al. | |
| 2006/0089656 A1 | 4/2006 | Allard et al. | |
| 2006/0111779 A1 | 5/2006 | Petersen | |
| 2006/0129247 A1 | 6/2006 | Brown et al. | |
| 2006/0142772 A1 | 6/2006 | Ralph et al. | |
| 2006/0161163 A1 | 7/2006 | Shino | |
| 2006/0178673 A1 | 8/2006 | Curran | |

(56) References Cited

U.S. PATENT DOCUMENTS

| | | |
|---|---|---|
| 2006/0217717 A1 | 9/2006 | Whipple |
| 2006/0241776 A1 | 10/2006 | Brown et al. |
| 2006/0271054 A1 | 11/2006 | Sucec et al. |
| 2007/0066977 A1 | 3/2007 | Assell et al. |
| 2007/0083265 A1 | 4/2007 | Malone |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0219634 A1 | 9/2007 | Greenhalgh et al. |
| 2008/0065093 A1 | 3/2008 | Assell et al. |
| 2008/0065215 A1 | 3/2008 | Reiley |
| 2008/0109083 A1 | 5/2008 | Van Hoeck et al. |
| 2008/0154316 A1 | 6/2008 | Reiley |
| 2009/0043393 A1 | 2/2009 | Duggal et al. |
| 2009/0259261 A1 | 10/2009 | Reiley |
| 2009/0324678 A1 | 12/2009 | Thorne et al. |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0145461 A1 | 6/2010 | Landry et al. |
| 2010/0191292 A1 | 7/2010 | DeMeo et al. |
| 2010/0280622 A1 | 11/2010 | McKinley |
| 2010/0292738 A1 | 11/2010 | Reiley |
| 2011/0029019 A1 | 2/2011 | Ainsworth et al. |
| 2011/0040362 A1 | 2/2011 | Godara et al. |
| 2011/0060375 A1 | 3/2011 | Bonutti |
| 2011/0087294 A1 | 4/2011 | Reiley |
| 2011/0087296 A1 | 4/2011 | Reiley et al. |
| 2011/0118785 A1 | 5/2011 | Reiley |
| 2011/0118790 A1 | 5/2011 | Reiley |
| 2011/0118796 A1 | 5/2011 | Reiley et al. |
| 2011/0118841 A1 | 5/2011 | Reiley |
| 2011/0125268 A1 | 5/2011 | Reiley |
| 2011/0153018 A1 | 6/2011 | Walters et al. |
| 2012/0179256 A1 | 7/2012 | Reiley |
| 2013/0131739 A1 | 5/2013 | Reiley |
| 2013/0184769 A1 | 7/2013 | Reiley et al. |
| 2013/0289625 A1 | 10/2013 | Reiley |
| 2014/0222150 A1 | 8/2014 | Reiley |
| 2014/0249589 A1 | 9/2014 | Reiley et al. |
| 2014/0257298 A1 | 9/2014 | Reiley |
| 2014/0257415 A1 | 9/2014 | Reiley |
| 2014/0330382 A1 | 11/2014 | Mauldin |
| 2015/0238205 A1 | 8/2015 | Reiley |
| 2015/0250595 A1 | 9/2015 | Mauldin et al. |

FOREIGN PATENT DOCUMENTS

| | | |
|---|---|---|
| CN | 1909848 A | 2/2007 |
| EP | 1287796 A1 | 3/2003 |
| JP | 05-176942 A | 7/1993 |
| JP | 2004121841 | 4/2004 |
| JP | 2004512895 | 4/2004 |
| JP | 2004516866 | 6/2004 |
| JP | 2006506181 | 2/2006 |
| WO | WO97/31517 A2 | 8/1997 |
| WO | WO02/38054 | 5/2002 |
| WO | WO03/007839 A2 | 1/2003 |
| WO | WO2004/002344 | 1/2004 |
| WO | WO2005/009729 A2 | 2/2005 |
| WO | WO2006003316 | 1/2006 |

OTHER PUBLICATIONS

Mauldin et al.; U.S. Appl. No. 13/791,746 entitled "Integrated implant," filed Mar. 8, 2013.

Mauldin, R. G.; U.S. Appl. No. 13/791,801 entitled "Threaded implant," filed Mar. 8, 2013.

Mauldin, R. G.; U.S. Appl. No. 13/791,837 entitled "Artificial joint," filed Mar. 8, 2013.

Mauldin, R. G.; U.S. Appl. No. 13/791,849 entitled "Revision tool and method," filed Mar. 8, 2013.

Mauldin et al.; U.S. Appl. No. 13/794,542 entitled "Tissue dilator and protector," filed Mar. 11, 2013.

Mauldin et al.; U.S. Appl. No. 13/794,580 entitled "Guide pin," filed Mar. 11, 2013.

Mauldin et al.; U.S. Appl. No. 13/794,611 entitled "Impactor," filed Mar. 11, 2013.

Reiley, Mark.; U.S. Appl. No. 13/858,814 entitled "Apparatus, systems, and methods for achieving trans-iliac lumbar fusion," filed Apr. 8, 2013.

Reiley, Mark; U.S. Appl. No. 13/867,941 entitled "Apparatus, systems, and methods for achieving anterior lumbar interbody fusion," filed Apr. 22, 2013.

Mauldin et al.; U.S. Appl. No. 13/888,249 entitled "Fenestrated Implant," filed May 6, 2013.

Reiley, Mark; U.S. Appl. No. 13/898,415 entitled "Apparatus, systems, and methods for achieving lumbar facet fusion," filed May 20, 2013.

Reiley, Mark A.; U.S. Appl. No. 14/162,689 entitled "Systems and methods for the fixation or fusion of bone," filed Jan. 23, 2014.

Mauldin et al.; U.S. Appl. No. 14/216,790 entitled "Systems and methods for implanting bone graft and implant," filed Mar. 17, 2014.

Mesiwala et al.; U.S. Appl. No. 14/216,863 entitled "Implants for spinal fixation or fusion," filed Mar. 17, 2014.

Yerby et al.; U.S. Appl. No. 14/216,938 entitled "Implants for facet fusion," filed Mar. 17, 2014.

Schneider et al.; U.S. Appl. No. 14/217,008 entitled "Systems and methods for removing an implant," filed Mar. 17, 2014.

Yerby et al.; U.S. Appl. No. 14/217,089 entitled "Long implant for sacroiliac joint fusion," filed Mar. 17, 2014.

Reiley; U.S. Appl. No. 14/488,144 entitled "Systems and methods for the fixation of bone," filed Sep. 16, 2014.

Reckling et al.; U.S. Appl. No. 14/515,416 entitled "Implant Placement," filed Oct. 15, 2014.

Acumed; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.

Peretz et al.; The internal bony architecture of the sacrum; Spine; 23(9); pp. 971-974; May 1, 1998.

Schneider et al.; U.S. Appl. No. 14/859,005 entitled "Matrix implant," filed Sep. 18, 2015.

Reiley et al.; U.S. Appl. No. 14/859,046 entitled "Implants for bone fixation or fusion," filed Sep. 18, 2015.

* cited by examiner

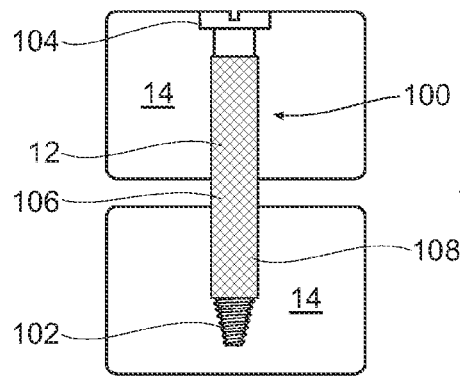
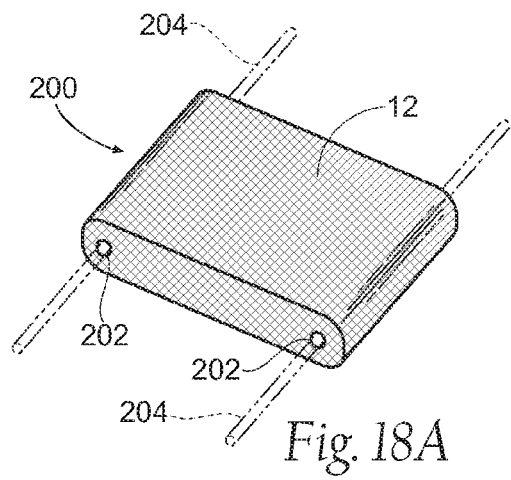
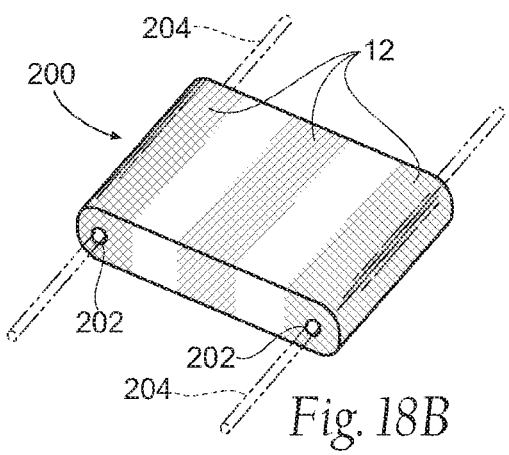
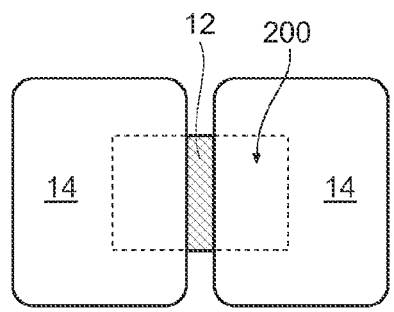
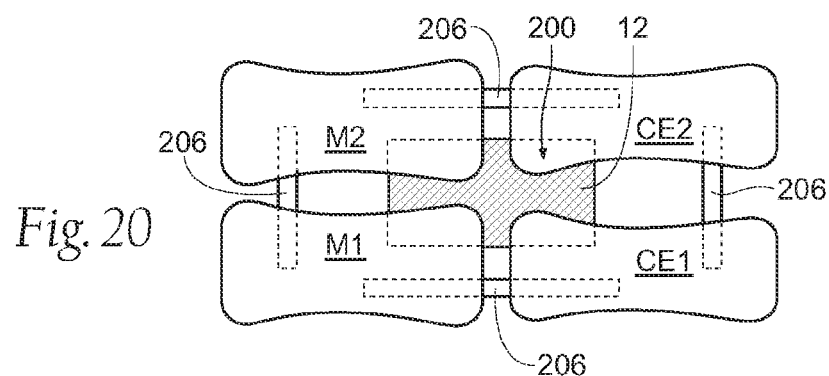

SYSTEMS AND METHODS FOR THE FIXATION OR FUSION OF BONE

RELATED APPLICATIONS

This application is a continuation of co-pending application Ser. No. 12/804,516 filed 22 Jul. 2010, which is a divisional of patent application Ser. No. 11/136,141, filed May 24, 2005, which is a continuation-in-part of U.S. patent application Ser. No. 10/914,629, filed Aug. 9, 2004.

FIELD OF THE INVENTION

This application relates generally to the fixation of bone.

BACKGROUND OF THE INVENTION

Many types of hardware are available both for fracture fixation and for the fixation of bones that are to fused (arthrodesed).

Metal and absorbable screws are routinely used to fixate bone fractures and osteotomies. It is important to the successful outcome of the procedure that the screw is able to generate the compressive forces helpful in promoting bone healing.

SUMMARY OF THE INVENTION

The invention provides bone fixation/fusion devices and related methods for stabilizing bone segments, which can comprise parts of the same bone (e.g., fracture fixation) or two or more individual bones (e.g., fusion). The systems and methods include a fixation/fusion device adapted for placement in association with bone segments.

One aspect of the invention provides a method comprising identifying a bone site comprising a first bone segment, a second bone segment, and a joint between the first and second bone segments. The method includes providing an elongated bone fusion device having a rectilinear cross section and including an exterior surface treated to provide bony in-growth, the elongated bone fusion device including a lumen accommodating passage over a guide pin. The method includes forming a bore in the first bone segment, and forming a bore in the second bone segment that faces the bore in the first bone segment across the joint. The bores in the first and second segments are each sized and configured to tightly engage the exterior surface of the elongated bone fusion device. The method includes placing in the bore of the first bone segment a guide pin that extends across the joint into the bore of the second bone segment. The method includes fusing the joint by passing the elongated bone fusion device over the guide pin across the joint and into tight engagement within the bores of the first and second bone segments, to thereby restrict movement of the elongated bone fusion device across the joint and provide bony in-growth within the bores along the exterior surface of the bone fusion device. The method includes removing the guide pin.

Another aspect of the invention provides a joint fusion device comprising an elongated device having a rectilinear cross section free of screw threads and being sized and configured for placement in association with a joint between individual first and second bone segments in response to an axially applied, non-rotational force. The elongated bone fusion device includes a lumen to accommodate passage over a guide pin during placement and an exterior surface treated to provide bony in-growth upon placement.

In one embodiment, the rectilinear cross section of the elongated bone fusion device comprises a square.

In one embodiment, the rectilinear cross section of the elongated bone fusion device comprises a rectangle.

In one embodiment, the rectilinear cross section of the elongated bone fusion device comprises a triangle.

BRIEF DESCRIPTION OF THE DRAWINGS

FIG. 17 is a top plan view of a bone fixation/fusion device positioned in association with a fracture line or between different bone segments.

FIG. 18A is a perspective view of an alternative embodiment of a bone fixation/fusion device having a bony in-growth and/or bony through-growth region that extends substantially along the entire device.

FIG. 18B is a perspective view of a bone fixation/fusion device similar to FIG. 18A and having a bony in-growth and/or bony through-growth region that extends along a portion of the device.

FIG. 19 is a top plan view of the bone fixation/fusion device of FIG. 18A in positioned in association with a fracture line or between different bone segments.

FIG. 20 is a top plan view of the bone fixation/fusion device of FIG. 18A positioned in association with a fracture line or between different bone segments and stabilized by fixation screws.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1A:
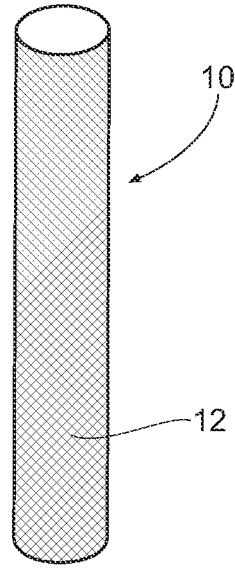
FIGS. 1A and 1B are perspective alternative views of a bone fixation/fusion device having a bony in-growth and/or through-growth region of a mesh configuration.
Figure 1B:
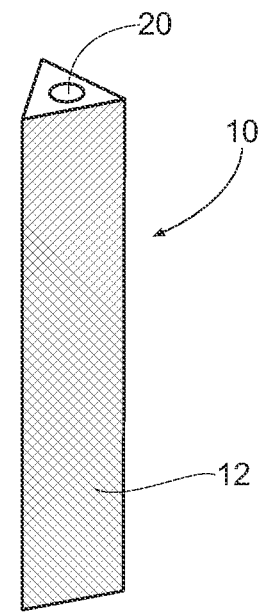

FIGS. 1A and 1B show representative alternative configurations of a device 10 sized and configured for the fixation of bone fractures (i.e., fixation of parts of the same bone) or for the fixation of bones which are to be fused (arthrodesed) (i.e. fixation of two or more individual bones that are adjacent and/or jointed). For the sake of shorthand, the device will sometimes be called a bone fixation/fusion device, to indicate that it can perform a fixation function between two or more individual bones), or a fusion function between two or more parts of the same bone, or both functions. As used herein, "bone segments" or "adjacent bone regions" refer to either situation, i.e., a fracture line in a single bone or a space between different bone segments.

In the embodiments shown in FIGS. 1A and 1B, the bone fixation/fusion device 10 comprises an elongated, stem-like structure. The device 10 can be formed—e.g., by machining, molding, or extrusion—from a material usable in the prosthetic arts, including, but not limited to, titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the device 10 may be formed from a suitable durable biologic material or a combination of metal and biologic material, such as a biocompatible bone-filling material. The device 10 may be molded from a flowable biologic material, e.g., acrylic bone cement, that is cured, e.g., by UV light, to a non-flowable or solid material.

The bone fixation/fusion device 10 can take various shapes and have various cross-sectional geometries. The device 10 can have, e.g., a generally curvilinear (i.e., round or oval) cross-section—as FIG. 1A shows—or a generally rectilinear cross section (i.e., square or rectangular or triangular—as FIG. 1B shows for purposes of illustration), or combinations thereof. As will be described in greater detail later (see, e.g., FIGS. 21A to 21F), instead of being shaped like an elongated stem, the body of the bone fixation/fusion device 10 can be less elongated and form more of a flattened, "wafer" configuration, having, e.g., a rectangular, square, or disc shape.

Figure 3:
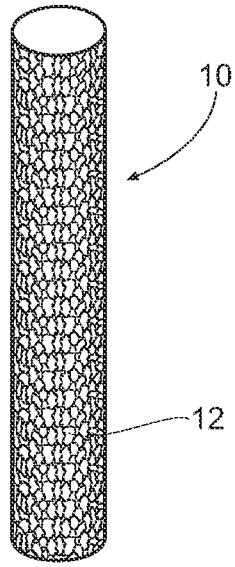
FIG. 3 is a perspective view of an alternative embodiment of a bone fixation/fusion device having a bony in-growth and/or through-growth region of a trabecular configuration.
Figure 2:
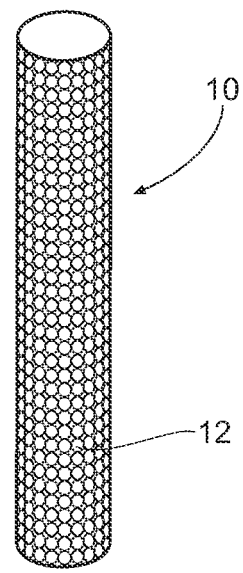
FIG. 2 is a perspective view of an alternative embodiment of a bone fixation/fusion device having a bony in-growth and/or through-growth region of a beaded configuration.

As FIGS. 2 and 3 show, the bone fixation/fusion device 10 desirably includes a region 12 formed along at least a portion of its length to promote bony in-growth onto or into surface of the device 10 and/or bony growth entirely through all or a portion of the device 10.

The region 12 can comprise, e.g., through holes, and/or various surface patterns, and/or various surface textures, and/or pores, or combinations thereof. The device 10 can be coated or wrapped or surfaced treated to provide the bony in-growth or through-growth region 12, or it can be formed from a material that itself inherently possesses a structure conducive to bony in-growth or through-growth, such as a porous mesh, hydroxyapetite, or other porous surface. The device 10 may further be covered with various other coatings such as antimicrobial, antithrombotic, and osteoinductive agents, or a combination thereof. The region 12 may be impregnated with such agents, if desired.

The configuration of the region 12 can, of course, vary. By way of examples, FIG. 1 shows the region 12 as an open mesh configuration; FIG. 2 shows the region 12 as beaded configuration; and FIG. 3 shows the region 12 as a trabecular configuration. Any configuration conducive to bony in-growth and/or bony through-growth will suffice.

Figure 4:
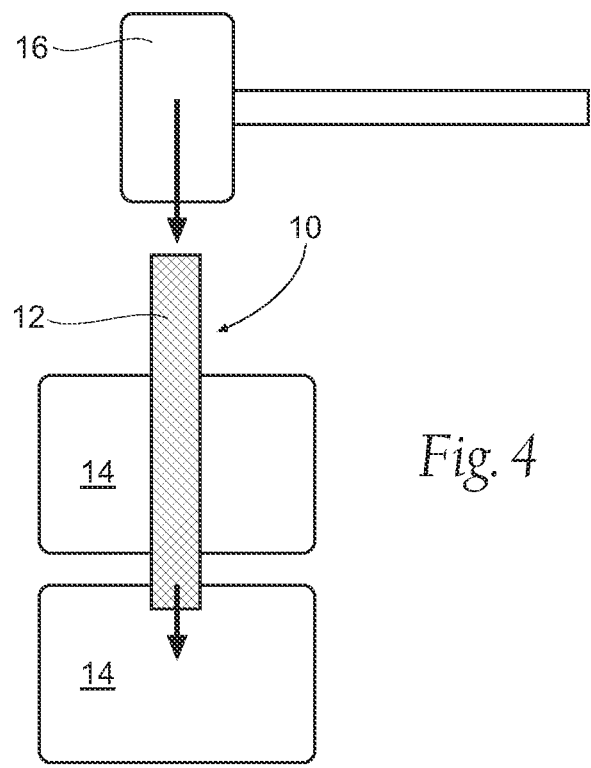
FIG. 4 is a schematic view of a bone fixation/fusion device of the type shown in FIG. 1, being inserted in association with bone across a fracture line or between different bone segments.

In use (see FIGS. 4 and 5), the bone fixation/fusion device 10 is inserted into a space between two adjacent bone surfaces, e.g., into a fracture site in a single bone or between two bones (e.g., adjacent vertebral bodies) which are to be fused together. In FIG. 4, the device 10 is shown being tapped into bone through bone segments 14 (i.e., across a fracture line or between adjacent bones to be fused) with a tap 16. The bone may be drilled first to facilitate insertion of the device 10. The bony in-growth or through-growth region 12 along the surface of the device 10 accelerates bony in-growth or through-growth onto, into, or through the device 10. Bony in-growth or through-growth onto, into, or through the device 10 helps speed up the fusion process or fracture healing time.

Figure 5:
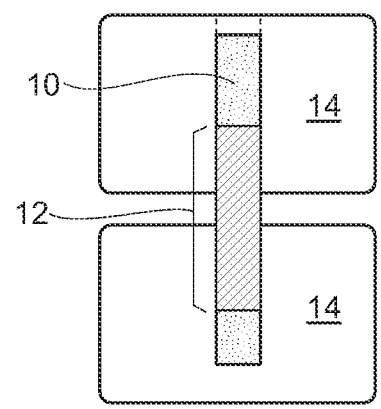
FIG. 5 is a schematic view of a bone fixation/fusion device positioned in association with a fracture line or between different bone segments with a bony in-growth and/or through growth region extending across the fracture line or space between different bone segments.

The bony in-growth or through-growth region 12 may extend along the entire outer surface of the device 10, as shown in FIG. 4, or the bony in-growth or through-growth region 12 may cover just a specified distance on either side of the bone segments or fracture line, as shown in FIG. 5.

The size and configuration of the device 10 can be varied to accommodate the type and location of the bone to be treated as well as individual anatomy.

Figure 6:
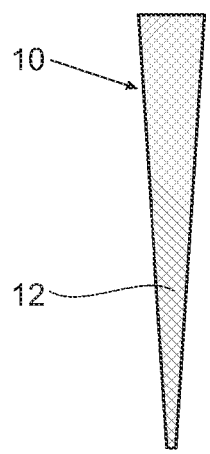
FIG. 6 is a front plan view of an alternative embodiment of a bone fixation/fusion device having a bony in-growth and/or bony through-growth region, in which the device has a conical configuration.
Figure 7:
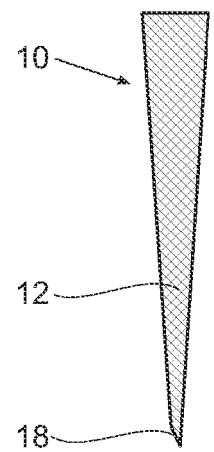
FIG. 7 is front plan view of an alternative embodiment of a bone fixation/fusion device having a bony in-growth and/or through-growth region in which the device has a beveled distal tip.
Figure 8A:
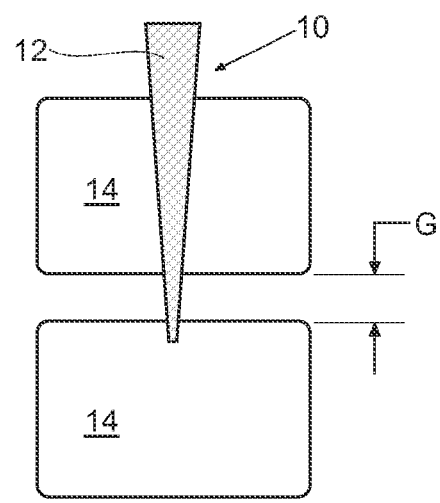
FIGS. 8A and 8B are schematics illustrating the insertion of a bone fixation/fusion device of the type shown in FIG. 6 in association with a fracture line or between different bone segments.
Figure 8B:
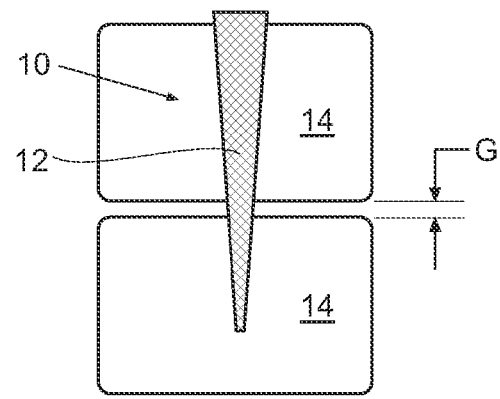

As FIG. 6 shows, the device 10 can be angled or tapered in a conical configuration. The degree of angle can be varied to accommodate specific needs or individual anatomy. A lesser degree of angle (i.e., a more acute angle) decreases the risk of splitting the bone as the device 10 is tapped into the bone or the fracture segments 14. The device 10 may also include a beveled distal tip 18 to further add in insertion of the device 10 into bone, as shown in FIG. 7. As shown in FIGS. 8A and 8B, the conical shape also helps drive the bone segments or fracture fragments together, reducing the gap (G) between the bone segments 14 or fracture segments.

In FIGS. 9 to 12, the device 10 is cannulated, having a central lumen or throughbore 20 extending through it, to assist in the placement of the device 10 within bone. FIG. 1B also shows a cannulated throughbore 20 in a different configuration.

Figure 9:
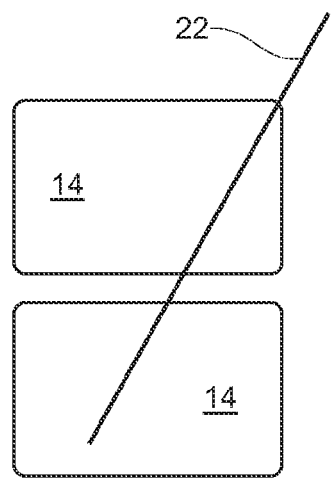
FIG. 9 is a schematic illustrating a guidewire being introduced into bone in association with a fracture line or between different bone segments.
Figure 10:
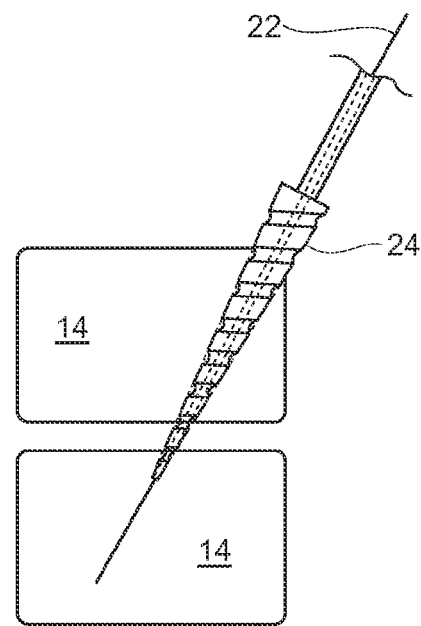
FIG. 10 is a schematic similar to FIG. 9 and illustrating a drill bit being introduced over the guidewire.
Figure 11:
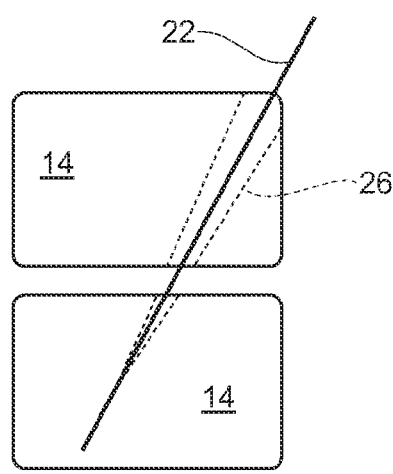
FIG. 11 is a schematic similar to FIG. 10 and illustrating a bore formed in the bone remaining after withdrawal of the drill bit.
Figure 12:
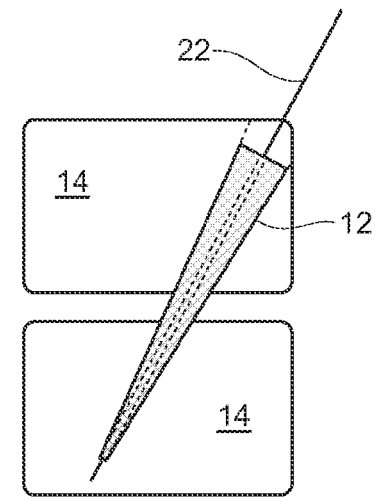
FIG. 12 is a schematic similar to FIG. 11 and illustrating insertion of a bone fixation/fusion device into the preformed bore.

In use, the physician can insert a conventional guide pin 22 through the bone segments 14 by conventional methods, as FIG. 9 shows. A cannulated drill bit 24 can then be introduced over the guide pin 22, as seen in FIG. 10. A single drill bit or multiple drill bits 24 can be employed to drill through bone fragments or bone surfaces to create a bore 26 of the desired size and configuration. In the illustrated embodiment, the drill bit 24 is sized and configured to create a conical bore 26 similar in size and configuration to the device 10. The bore 26 is desirably sized and configured to permit tight engagement of the device 10 within the bore 26 and thereby restrict movement of the device 10 within the bore 26. The pre-formed bore 26 may be slightly smaller than the device 10, while still allowing the device 10 to be secured into position within the bore 26 by tapping. As seen in FIG. 11, the drill bit 24 is then withdrawn. The device 10 is then inserted into the bore 26 over the guide pin 22, as FIG. 12 shows. The guide pin 22 is then withdrawn.

Alternatively, the bone fixation/fusion device 10 itself can include screw-like threads along the body for screwing the device into place. In the arrangement, the device 10 be self-tapping. Also in this arrangement, the device 10 can be cannulated for use with a guide pin 22, or it need not be cannulated.

Multiple devices 10 may be employed to provide additional stabilization. While the use of multiple devices 10 will now be described illustrating the use of multiple devices 10 of the same size and configuration, it is contemplated that the devices 10 may also be of different size and/or configuration, e.g., one device 10 is of a cylindrical configuration and a second device 10 is of a conical configuration.

Figure 13:
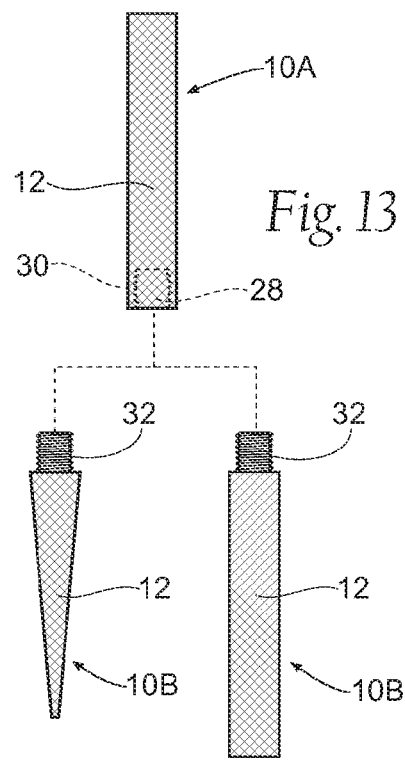
FIG. 13 is an exploded front plan view illustrating the coupling of a pair of bone fixation/fusion by threaded engagement.

In many cases, it may be desirable to couple a series of devices 10 together, e.g., to provide stabilization over a larger surface area. A series of devices 10 may be coupled together be any suitable means, e.g., by a snap fit engagement, or a groove and tab key arrangement, or by a Morse taper fit, or combinations thereof. In one embodiment, a series of devices 10 are coupled by threaded engagement. As illustrated in FIG. 13, a first device 10A includes a recess 28 at one end providing a series of internal threads 30. In the illustrated embodiment, the first device 10 is of a cylindrical configuration, but may be of any desired configuration. The internal threads 30 couple with a series of complementary external threads 32 on a second device 10B of a similar or of a different configuration to couple the first and second devices 10A and 10B together.

Figure 14:
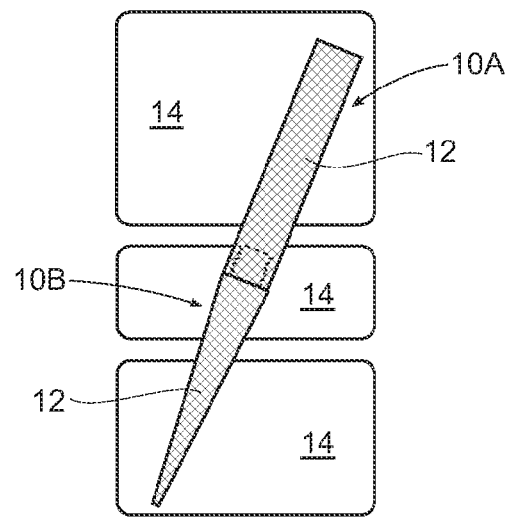
FIG. 14 is a schematic illustrating a pair of bone fixation/fusion devices coupled together and inserted in association with a fracture line or between different bone segments.

The devices 10A and 10B are desirably coupled together prior to being inserted into the pre-formed bore 26. The series of internal and external threads 30 and 32 provide an interlocking mechanism that permits a series of devices 10 to be stacked and connected to cover a larger area or multiple bone segments 14 (e.g., a bone having multiple fractures) and thereby provides additional stabilization, as seen in FIG. 14.

Figure 15:
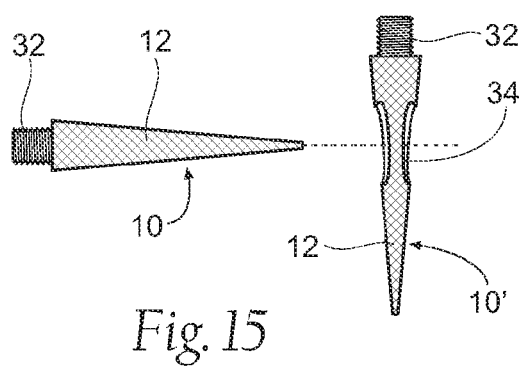
FIG. 15 is a front plan view illustrating passage of a bone fixation/fusion device through a fenestration in another bone fixation/fusion device.

FIG. 15 illustrates another embodiment in which a device 10' includes an opening or fenestration 34 to allow another device 10 to pass through, thereby providing additional stabilization. The fenestration 34 can be sized and configured to permit another device 10 to be passed through the device 10' at virtually any angle. The fenestration 34 can also be sized and configured to limit movement of the second device 10 relative to the second device 10'.

Figure 16:
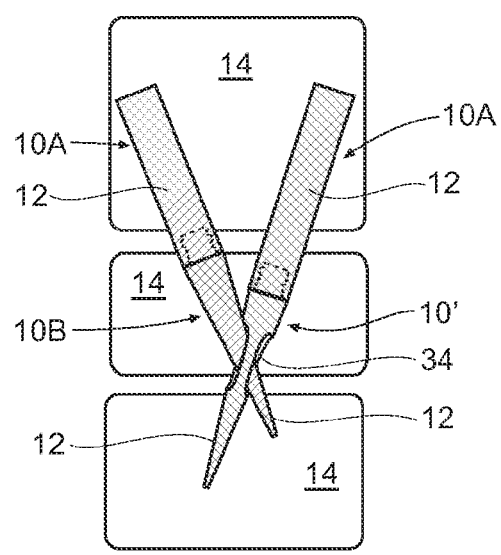
FIG. 16 is a schematic illustrating the placement of a series of bone fixation/fusion devices in bone.

In use, and as shown in FIG. 16, the physician taps a first device 10' having a fenestration 34 through the bone segments. A second device 10 is then inserted (e.g., by tapping) through the fenestration 34 of the first device 10' into place.

It is further contemplated that device 10' may also be adapted for coupling with another device 10A (e.g., by a series of external and internal threads), permitting the devices 10' and 10A to be additionally stacked and connected, as also shown in FIG. 16.

FIG. 17 illustrates an alternative form of a bone fixation/fusion device 100. Similar to the type of bone fixation/fusion device 10 previously described, device 100 includes a body 106 formed of a durable material that is not subject to significant bio-absorption or resorption by surrounding bone or tissue over time. In other words, the body 106 is intended to remain in place for a time sufficient to stabilize the fracture or fusion site. Such materials are well know in the prosthetic arts and include, e.g., titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the body 106 of the bone fixation/fusion device 100 may be formed from a suitable durable biologic material or a combination of metal and biologic material, such as a biocompatible bone-filling material. The body 106 of the device 100 may be molded from a flowable biologic material, e.g., acrylic bone cement, that is cured, e.g., by UV light, to a non-flowable or solid material.

The body 106 of the device 100 may also include a bony in-growth or through-growth region 108, as already described in association with previous embodiments.

Unlike the bone fixation/fusion device 10, the bone fixation/fusion device 100 includes at least one region associated with the body 106 that, in contrast to the body 106, comprises a material that is subject to more rapid in vivo bio-absorption or resorption by surrounding bone or tissue over time, e.g., within weeks or a few months. The resorbable material can comprise, e.g., polylactic acid (PLA), polyglycolic acid (PGA), poly(lactideglycolide) copolymers, polyanliydrides, cyclode, cirsns, polyorthoasters, n-vinyl alcohol, or other biosorbable polymers or like materials known or recognized in the prosthetic arts as having such characteristics. The bio-absorbable region is intended to facilitate implantation or placement of the body 106, but over time be absorbed to minimize the footprint of the implanted device 100 in the long run.

The bioabsorbable region or regions can possess functionality to aid in the implantation process. For example, as shown the illustrated embodiment, there are two bioabsorbable regions 102 and 104. Region 102 comprises a bioabsorbable screw region 102, which is desirably threaded or otherwise suitably configured to pierce bone and facilitate advancement of the device 100 into bone. The other region 104 comprises a bioabsorbable head region 104, which is desirably configured to mate with an installation instrument, e.g., a screwdriver, to further facilitate advancement and positioning of the bone fixation/fusion device 100 in bone. The bioabsorbable head 104 may also be sized and configured to temporarily anchor the device 100 within bone, e.g., the head 104 may be a slightly larger diameter than the body 106 of the device 100. The bioabsorbable screw portion 102 and head portion 104 are configured to provide an immediate benefit during the initial placement or position of the device 100, but over time be resorbed when they have served their initial purpose during implantation. This leaves the more durable and less resorbable body 106 behind, to serve its longer-term function of stabilizing the fracture or fusion site.

As previously disclosed, a given bone fixation/fusion device can take various shapes and geometries. For example, as shown in FIGS. 18A and 18B, the bone fixation/fusion device 200 possesses a flattened rectangular (or wafer-like) configuration. A region 12 of the device 200 can be textured or treated, as previously described, to provide bony in-growth or through-growth. The bony in-growth or through-growth region 12 may extend along the entire device 200 (see FIG. 18A) or along any portion or portions of the device 200 (see FIG. 18B).

The bone fixation/fusion device 200 is desirably sized and configured to be positioned to join two or more adjacent bone segments 14 (which can comprise a fracture site, a fusion site, or both), as FIG. 19 shows, to fix and to promote the fusion of the adjacent bone segments 14. The device 200 may also be sized and configured to fix and to promote fusion of multiple bone segments 14 or compound fractures, as FIG. 20 shows. FIG. 20 illustrates placement of the bone fixation/fusion device 200 sized and configured for the fixation and fusion of, for example, a first cuneiform (CE1), a second cuneiform (CE2), a first metatarsal (M1), and a second metatarsal (M2).

As shown in FIG. 20, one or more auxiliary fixation elements, such as conventional orthopedic screws 206, may also be placed within and/or across the bone segments 14 by conventional techniques, to augment the stabilization of the bone segments 14 during the fusion process.

Figure 21A:
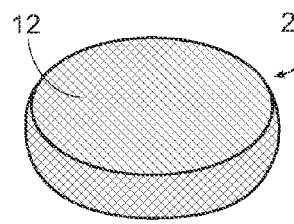
FIGS. 21A to 21F are perspective views illustrating alternative configurations of bone fixation/fusion devices of a type shown in FIG. 18A.
Figure 21B:
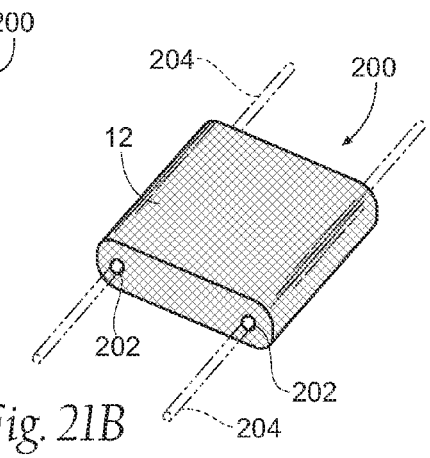
Figure 21C:
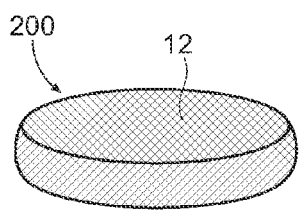
Figure 21D:
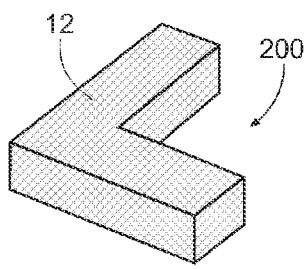
Figure 21E:
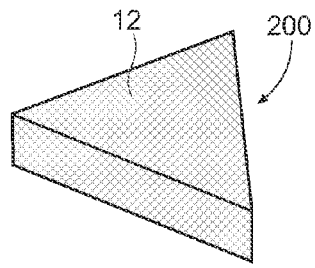
Figure 21F:
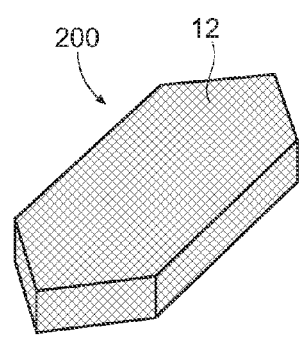

The size and configuration of the bone fixation/fusion device 200 may be modified or adjusted in diverse ways to serve the intended stabilization function in diverse bone locations, bone geometries, or bone types, which are intended to be fused or repaired. The bone fixation/fusion device 200 can come in a family of different pre-established sizes and shapes, or it can be individually sized and configured to meet the requirements of a particular individual's anatomy. For the sake of illustration, by not limitation, a given bone fixation/fusion device 200 may take the form of a disc (FIG. 21A), a square (FIG. 21B), or an oval (FIG. 21C). The height, width, and length of a given bone fixation/fusion device 200 may be varied depending on the specific location and amount of bone to be crossed for stabilization. A given bone fixation/fusion device may possess a symmetric geometry, or an asymmetric or complex geometry—such as an L shape (FIG. 21D), a triangle (FIG. 21E), or rectangle with a triangular ends (FIG. 22F). Any combination of linear or curvilinear or rounded geometries is possible.

Figure 24:
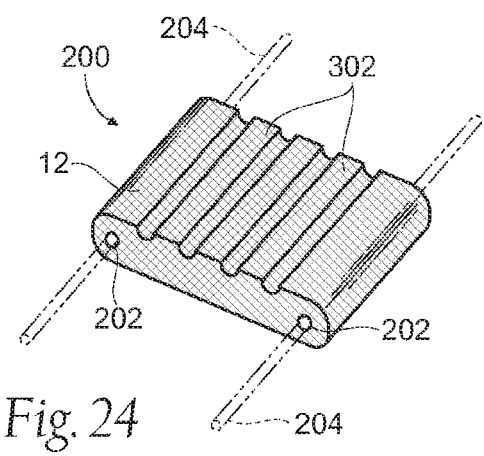
FIG. 24 is a perspective view illustrating an alternative embodiment of the bone fixation/fusion device of a type shown FIG. 18A in which the device includes a series of grooves providing an anti-rotational function.

As before described, a given bone fixation/fusion device can be cannulated to aid in guidance during placement or implantation. For example, as shown in FIGS. 18A and 18B, the device 200 can include a pair of opposing guide bores 202. The guide bores 202 are sized and configured to accommodate passage of guide pins 204, which are secured at the intended site of device placement. Other forms of cannulated devices 200 are shown in FIGS. 21B and 24. In this way, the bone fixation/fusion device 200 can be guided by the pins 204 to the intended bone placement site.

Figure 22A:
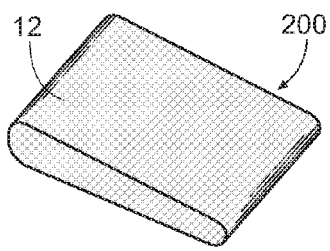
FIGS. 22A and 22B are perspective views illustrating alternative embodiments of the bone fixation/fusion of a type shown in FIG. 18A in which the device is profiled.
Figure 22B:
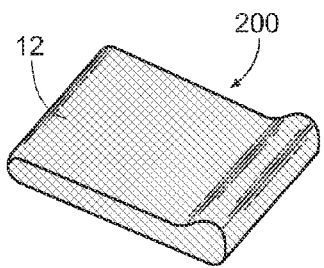

To aid in stabilizing a given bone fixation/fusion device within bone, the device may be profiled. For example, as shown in FIG. 22A, the bone fixation/fusion device 200 may vary in height across its entire length of the device 200, to form a tapered wedge. Alternatively, as shown in FIG. 22B, the bone fixation/fusion device 200 may vary in height at one end only. In these arrangements, the bone fixation/fusion device 200 is desirably positioned with the area of greatest height in the proximal direction, which serves to wedge the device 200 into place within bone.

Figure 23A:
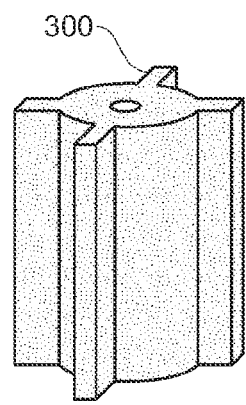
FIGS. 23A and 23B are perspective views illustrating alternative embodiments of the bone fixation/fusion device of a type shown in FIG. 1 with structural elements that provide an anti-rotational function.
Figure 23B:
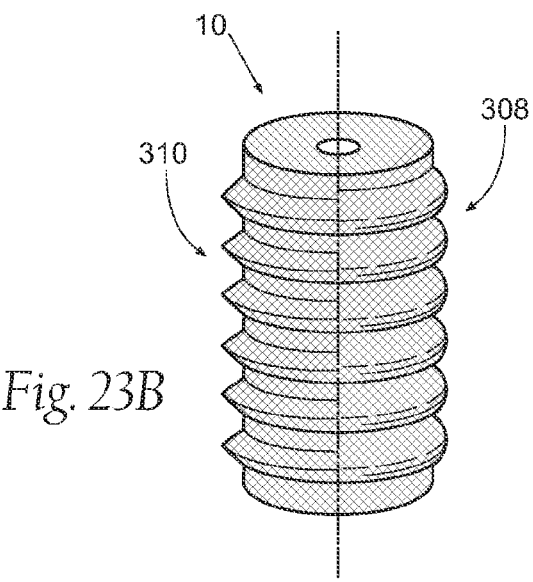
Figure 25:
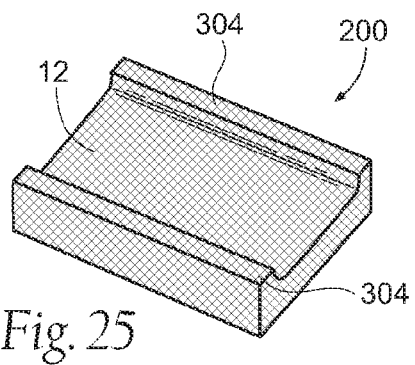
FIG. 25 is a perspective view illustrating an alternative embodiment of the bone fixation/fusion device of a type shown in FIG. 18A in which the device includes a pair of opposing wings providing an anti-rotational function.
Figure 26:
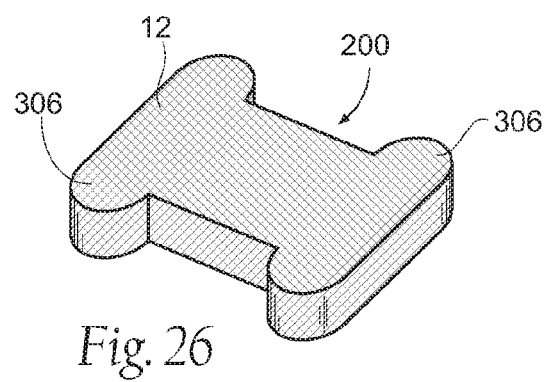
FIG. 26 is a perspective view illustrating an alternative embodiment of the bone fixation/fusion device of FIG. 18A in which the device includes a pair of opposing flanges providing an anti-rotational function.

To also aid in stabilizing a given bone fixation/fusion device within bone, the device can include one or more anti-rotational elements, which further stabilize and secure the device in the desired position within bone. The size and configuration of the anti-rotational elements may vary. For example, the anti-rotational elements may comprise an array of fins 300 projecting from a stem-like device 10 (FIG. 23A), or an array of grooves 302 formed in a rectangular wafer device 200 (FIG. 24), or wings 304 formed in a rectangular wafer device 200 (FIG. 25), or flanges 306 projecting from a wafer device 200 (FIG. 26). The anti-rotational elements can comprise (see FIG. 23B) an array of bumps 308 or surface projections 310 formed on all or a portion of the device, which can be either stem-like or wafer-like in its configuration. Any number of anti-rotational elements, or any configuration of anti-rotational elements, or any combinations of configurations can be provided to serve the functional objective of stabilization.

Figure 27:
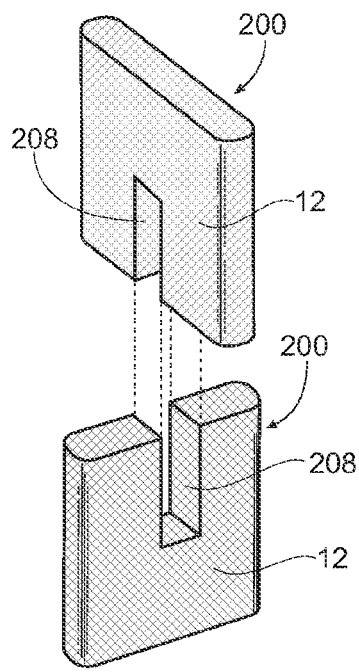
FIG. 27 is an exploded view of a pair of coupled bone fixation/fusion devices that, when fitted together, form a composite bone fixation/fusion device.
Figure 28:
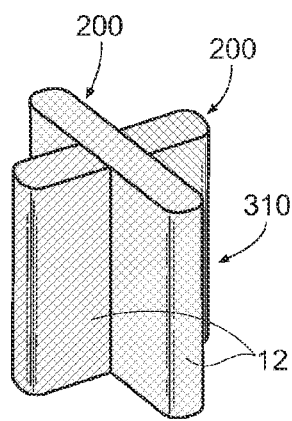
FIG. 28 is an assembled view of the composite bone fixation/fusion device formed from the assembly of the bone fixation/fusion devices shown in FIG. 27.
Figure 29:
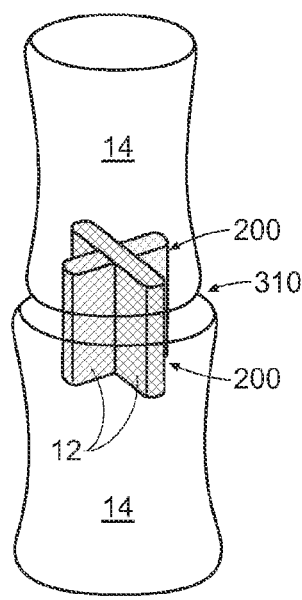
FIG. 29 is a front view of the assembled composite bone fixation/fusion device of FIG. 28 positioned in association with a fracture line or between different bone segments.

As also previously described, two or more bone fixation/fusion devices 200 of the types generally described above may be assembled to form a composite bone fixation/fusion device having a desired size and configuration. For example, in the arrangement shown in FIGS. 27 to 29, the bodies of two bone fixation/fusion devices 200 each have a slot 208. Slot 208 in a first device 200 mates with a like or complementary slot 208 in a second device 200 to permit the assembly of a composite bone fixation/fusion device 310, which has a crossed, anti-rotational configuration for placement across bone segments 14. The crossed relation of the composite bone fixation/fusion device 310 has an increased surface area and adds further stability to the devices 200 in bone during the fusion process.

It will be apparent to one of skill in the art that the location, size, and configuration of the slots 208 may be varied to accommodate specific needs and a specific anatomical location as well as individual anatomy. It is also apparent that other mating configurations, e.g., groove and tab fitments, or snap-fit arrangements, or Morse taper fits, or threaded assemblies, can be use to assemble two or more bone fixation/fusion devices into a composite device 310.

Figure 30:
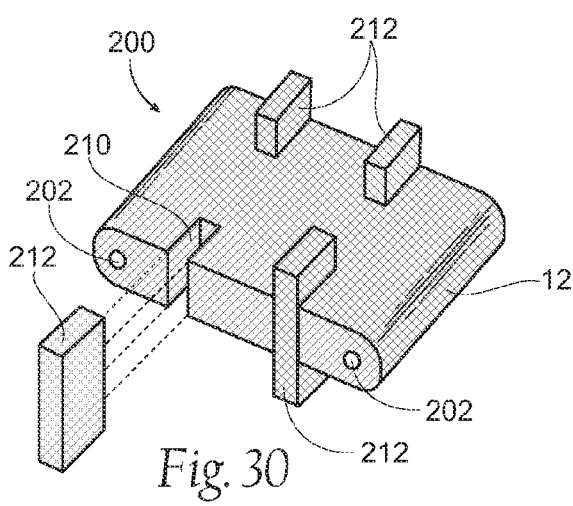
FIG. 30 is a perspective view of an alternative embodiment of the bone fixation/fusion device of a type shown in FIG. 18A with fixation plates.

As shown in FIG. 30, fixation or gripping plates 212 may be fitted to a given bone fixation/fusion device. In the arrangement shown in FIG. 30, the body of the bone fixation/fusion device 200 includes one or more attachment sites 210, e.g., slits or indentations, which are sized and configured to receive a selectively removable fixation or gripping plate 212. When received within the slit 210, the plate 212 extends radially from the device to grip into bone and further secure the device 200 within bone.

Figure 31:
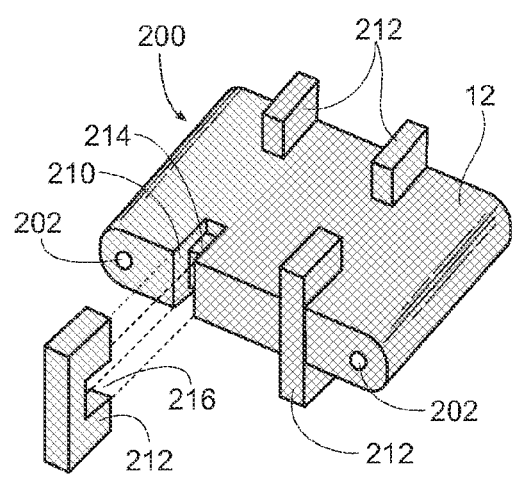
FIG. 31 is a perspective view of an alternative embodiment of the bone fixation/fusion device of FIG. 30.

In an alternative embodiment, shown in FIG. 31, the attachment site 210 can include a tab 214, which mates with a notch 216 in the fixation plate 212 to secure the plate 212 within the device 200.

Other forms of interlocking or nesting configuration can be used. For example, tongue-and-groove fitments, or snap-fit arrangements, or threaded fitments, or Morse taper assemblies can be use to assemble one or more fixation or gripping plates to a bone fixation/fusion device.

The fixation or gripping plate 212 is formed of durable biocompatible metal or bone substitute material, as previously described. In some cases, it may be desirable to provide a bony in-growth surface on at least a portion of the plate 212. Alternatively, the plate 212 may be formed of a bio-absorbable material, as already described.

Figure 32:
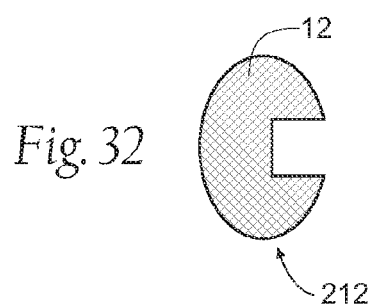
FIG. 32 is a side view of an alternative embodiment of a fixation plate having a rounded configuration.
Figure 33:
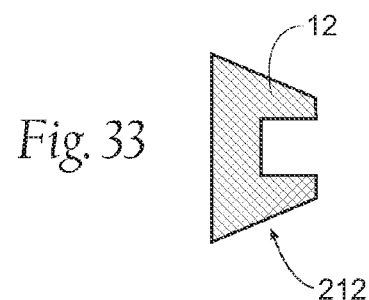
FIG. 33 is a side view of an alternative embodiment of a fixation plate having a tapered configuration.

FIGS. 30 and 31 illustrate embodiments in which the plates 212 present a generally blunt and flat configuration. It will be apparent to one of skill in the art that, however, that the plates 212 may also provide a sharpened or cutting edge or be otherwise sized and configured as necessary to accommodate specific location and individual anatomy. For example, the plate 212 may be rounded (FIG. 32) or tapered (FIG. 33).

Figure 34:
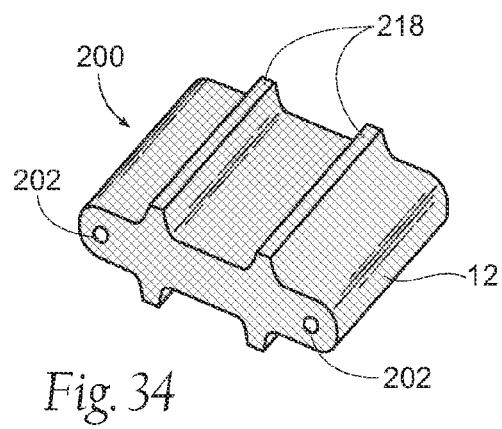
FIG. 34 is a perspective view of an alternative embodiment of the bone fixation/fusion device of a type shown in FIG. 18A providing a series of radially-extending fixation ridges.

FIG. 34 illustrates an alternative embodiment in which one or more fixation ridges 218 extend radially from the bone fixation/fusion device 200. Similar to the fixation plates 212, the ridges 218 may be variously sized and configured so as to grip into bone and further secure the bone fixation/fusion device 200 within bone.

Figure 35A:
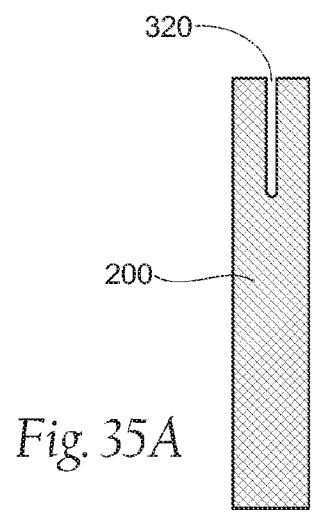
FIGS. 35A and 35B are perspective views of a bone fixation/fusion device having a malleable region that can be flared or expanded to provide fixation and/or anti-rotation resistance.
Figure 35B:
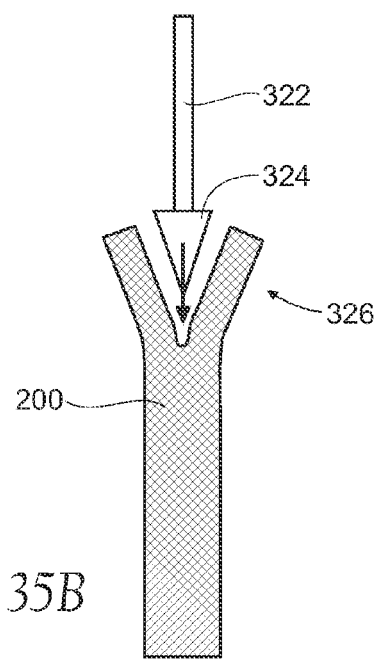

Fixation elements can be formed in situ. For example, as shown in FIG. 35A, a bone fixation/fusion device 200 can include a malleable region 320 that normally presents a low-profile conducive to implantation. As FIG. 35B shows, the profile of the malleable region 320 can be changed in situ after implantation to a radially enlarged or extended profile 326 that provides stabilization or an anti-rotational function to the device 200. In the illustrated embodiment, the malleable region 320 is slotted (see FIG. 35A) to accommodate placement of a wedge tool 324 carried for manipulation by a stylet or cannula 322 (see FIG. 35B). The wedge tool 324 flays apart the slotted malleable region 320 (as FIG. 35B shows), to create the enlarged profile 326 for stabilization and/or rotation resistance.

Figure 36:
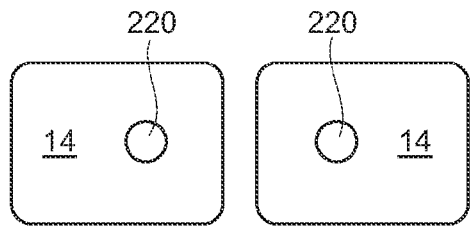
FIG. 36 is a front plan view illustrating the drilling of pilot holes in adjacent bone segments, which can comprise a fracture line in the same bone or different bone segments.

In use, and with reference to FIG. 36, pilot holes 220 are drilled into adjacent bone segments 14 (e.g., along a fracture line in a single bone or between adjacent segments of different bones) by conventional surgical techniques. In the illustrated embodiment, a single pilot hole 220 is drilled into each bone segment 14. It is to be understood that the number and configuration of the pilot holes 220 may vary as necessary or as desired.

Figure 37:
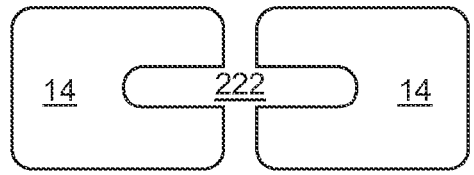
FIG. 37 is a front plan view illustrating a cavity bored between the pilot holes to receive a bone fixation/fusion device.

As shown in FIG. 37, the physician can then then saw, using conventional methods, between the pilot holes 220 to prepare a cavity 222 to receive the device 200.

Figure 38:
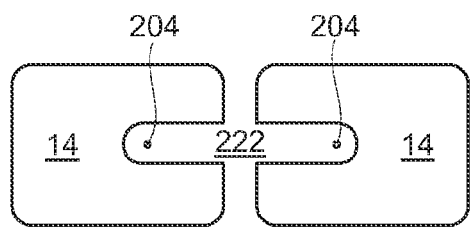
FIG. 38 is a front plan view illustrating the placement of a pair of guide pins within the bored cavity.
Figure 39:
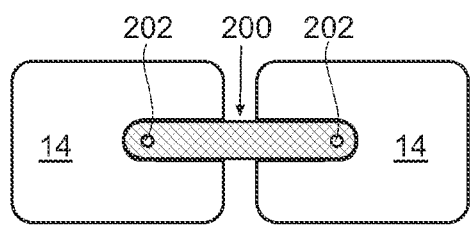
FIG. 39 is a front plan view illustrating the placement of the bone fixation/fusion device into the cavity and removal of the guide pins.

Guide pins 204 may, if desired, be placed at opposing ends of the bored cavity 222, as seen in FIG. 38. In this arrangement, as shown in FIG. 39, the selected bone fixation/fusion device 200 is passed over the guide pins 204 to position the device 200 with the cavity 222. The guide pins 204 may then be removed. In an alternative arrangement, guide pins 204 need not be used, and the device 200 is manually inserted by the physician into the bore cavity 222.

Figure 40:
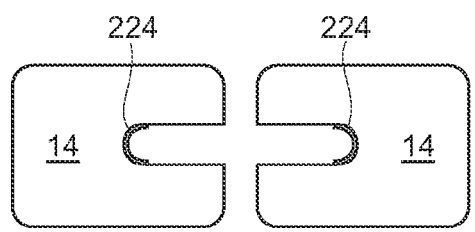
FIG. 40 is a front plan view illustrating the placement of a pair of opposing c-shaped restraints within the bored cavity.
Figure 41:
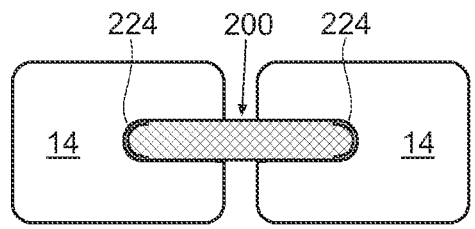
FIG. 41 is a front plan view illustrating the placement of the bone fixation/fusion device into the cavity within the restraints.

An alternative embodiment is illustrated in FIGS. 40 and 41. In this embodiment, a c-shaped restraint 224 is placed against each end of the bored cavity 222. The selected bone fixation/fusion device 200 is then positioned between the restraints 222 such that the restraints 222 engage the device 200 to secure the device 200 within bone.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:
1. A joint fusion device comprising:
an elongated bone fusion device having a proximal end, a distal end, a longitudinal axis and a substantially triangular cross section transverse to the longitudinal axis and free of external screw threads and being sized and configured for placement in association with and non-parallel to a joint between individual first and second bone segments in response to an axially applied, non-rotational force, the elongated bone fusion device including a lumen extending through the length of the elongated bone fusion device from the proximal end to the distal end and oriented parallel to the longitudinal axis to accommodate passage over a guide pin during placement and an exterior surface treated to provide bony in-growth upon placement, wherein the exterior surface has a rough surface texture, wherein the distal end includes a beveled distal tip.
2. A device according to claim 1, wherein the elongated bone fusion device is formed from one or more materials selected from the group consisting of metal, ceramic and glass.

3. A device according to claim 2, wherein the metal is selected from the group consisting of titanium, titanium alloys, tantalum, chrome cobalt and steel.

4. A device according to claim 1, wherein the rough surface texture is porous.

5. A device according to claim 1, wherein the rough surface texture is formed from an open mesh configuration.

6. A device according to claim 1, wherein the rough surface texture is formed from a beaded configuration.

7. A device according to claim 1, wherein the rough surface texture is formed from a trabecular configuration.

8. A device according to claim 1, wherein the exterior surface comprises at least one fenestration with an opening located on the exterior surface.

9. A device according to claim 1, wherein the elongated bone fusion device is sized to be the same cross-sectional size as a bore traversing the joint from the first bone segment to the second bone segment.

10. A device according to claim 1, wherein the elongated bone fusion device is sized to be slightly larger than the dimensions of a bore traversing the joint from the first bone segment to the second bone segment.

11. The device of claim 1, wherein the substantially triangular cross section transverse to the longitudinal axis remains substantially the same size along a majority of the length of the implant.

12. The device of claim 1, wherein the elongate bone fusion device is substantially straight from the proximal end to the distal end along the length of elongate bone fusion device.

13. A joint fusion device comprising:
an elongated bone fusion device having a proximal end, a distal end, a longitudinal axis and a cross section transverse to the longitudinal axis that is defined by at most three rounded apices, the elongated bone fusion device free of external screw threads and being sized and configured for placement in association with and non-parallel to a joint between individual first and second bone segments in response to an axially applied, non-rotational force, the elongated bone fusion device including a lumen extending through the length of the elongated bone fusion device from the proximal end to the distal end and oriented parallel to the longitudinal axis to accommodate passage over a guide pin during placement and an exterior surface treated to provide bony in-growth upon placement, wherein the exterior surface has a rough surface texture, wherein the distal end includes a beveled distal tip, wherein the elongated bone fusion device comprises a cross section transverse to the longitudinal axis that is defined by three rounded apices joined together by three sides.

14. The device of claim 13, wherein the three sides are curvilinear.

15. A joint fusion device comprising:
an elongated bone fusion device having a proximal end, a distal end, a longitudinal axis and a substantially triangular cross section transverse to the longitudinal axis and free of external screw threads and being sized and configured for placement in association with and non-parallel to a joint between individual first and second bone segments in response to an axially applied, non-rotational force, the elongated bone fusion device including a lumen extending through the length of the elongated bone fusion device from the proximal end to the distal end and oriented parallel to the longitudinal axis to accommodate passage over a guide pin during placement and an exterior surface treated to provide bony in-growth upon placement, wherein the exterior surface has a rough surface texture, wherein the lumen comprises internal screw threads located at least one end of the lumen.

\* \* \* \* \*